(12) United States Patent
Molinier et al.

(10) Patent No.: US 10,781,149 B2
(45) Date of Patent: Sep. 22, 2020

(54) TRANSALKYLATION PROCESS

(71) Applicant: ExxonMobil Chemical Patents Inc., Baytown, TX (US)

(72) Inventors: Michel Molinier, Houston, TX (US); Jeffrey L. Andrews, Houston, TX (US); Hari Nair, Somerville, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 26 days.

(21) Appl. No.: 14/941,720

(22) Filed: Nov. 16, 2015

(65) Prior Publication Data
US 2016/0176787 A1    Jun. 23, 2016

Related U.S. Application Data

(60) Provisional application No. 62/094,300, filed on Dec. 19, 2014.

(51) Int. Cl.
*C07C 6/12* (2006.01)
*C10G 29/20* (2006.01)

(52) U.S. Cl.
CPC ............ *C07C 6/126* (2013.01); *C10G 29/205* (2013.01); *C07C 2529/068* (2013.01); *C07C 2529/12* (2013.01); *C07C 2529/70* (2013.01); *C07C 2529/74* (2013.01); *C10G 2300/1096* (2013.01); *C10G 2400/30* (2013.01)

(58) Field of Classification Search
CPC .................................................... C07C 6/126
See application file for complete search history.

(56) References Cited

U.S. PATENT DOCUMENTS

| | | | |
|---|---|---|---|
| 3,293,192 A | 8/1965 | Maher et al. | |
| 3,308,069 A | 3/1967 | Wadlinger et al. | |
| 3,354,078 A | 11/1967 | Miale et al. | |
| 3,442,795 A | 5/1969 | Kerr et al. | |
| 3,449,070 A | 6/1969 | McDaniel et al. | |
| 3,524,820 A | 8/1970 | Hemminger | |
| 3,702,886 A | 11/1972 | Argauer et al. | |
| 3,709,979 A | 1/1973 | Chu | |
| 3,766,093 A | 10/1973 | Chu | |
| 3,832,449 A | 8/1974 | Rosinski et al. | |
| RE28,341 E | 2/1975 | Wadlinger et al. | |
| 3,894,104 A | 7/1975 | Chang et al. | |
| 3,923,636 A | 12/1975 | Mead et al. | |
| 3,972,983 A | 8/1976 | Ciric | |
| 4,016,218 A | 4/1977 | Haag et al. | |
| 4,016,245 A | 4/1977 | Plank et al. | |
| 4,076,842 A | 2/1978 | Plank et al. | |
| RE29,948 E | 3/1979 | Dwyer et al. | |
| 4,234,231 A | 11/1980 | Yan | |
| 4,375,573 A | 3/1983 | Young | |
| 4,401,556 A | 8/1983 | Bezman et al. | |
| 4,439,409 A | 3/1984 | Puppe et al. | |
| 4,556,477 A | 12/1985 | Dwyer | |
| 4,698,217 A | 10/1987 | Valyocsik | |
| 4,826,667 A | 5/1989 | Zones et al. | |
| 4,873,067 A | 10/1989 | Valyocsik et al. | |
| 4,954,325 A | 6/1990 | Rubin et al. | |
| 5,030,787 A | 7/1991 | Absil et al. | |
| 5,236,575 A | 8/1993 | Bennett et al. | |
| 5,250,277 A | 10/1993 | Kresge et al. | |
| 5,336,478 A | 8/1994 | Dwyer et al. | |
| 5,362,697 A | 11/1994 | Fung et al. | |
| 5,905,051 A | 5/1999 | Wu et al. | |
| 5,942,651 A | 8/1999 | Beech, Jr. et al. | |
| 6,706,937 B2 * | 3/2004 | Xiao ...................... | C07C 6/123 585/470 |
| 7,109,389 B2 * | 9/2006 | Kong ...................... | C07C 6/123 585/300 |
| 7,330,010 B2 | 2/2008 | Schroderus et al. | |
| 7,663,010 B2 | 2/2010 | Levin | |
| 8,183,424 B2 * | 5/2012 | Levin ..................... | B01J 29/064 585/323 |
| 2013/0066123 A1 * | 3/2013 | Lafyatis .................. | C07C 6/126 585/312 |

FOREIGN PATENT DOCUMENTS

WO    WO 2014/193563 A1    12/2014

OTHER PUBLICATIONS

Weisz, P. B., et al. "Superactive Crystalline Alluminosilicate Hydrocarbon Catalysts", Journal of Catalysis, vol. 4, Issue 4, pp. 527-529, Aug. 1965.
Miale, J. N., et al., "Catalysis by Crystalline Aluminosilicates, IV. Attainable Catalytic Cracking Rate Constants, and Superactivity" Journal of Catalysis, vol. 6, Issue 2, pp. 278-287, Oct. 1966.
Olson, D. H., et al., "Chemical and Physical Properties of the ZSM-5 Substitutional Series", Journal of Catalysis, vol. 61, Issue 2, pp. 390-396, Feb. 1980.

* cited by examiner

*Primary Examiner* — In Suk C Bullock
*Assistant Examiner* — Alyssa L Cepluch

(57) ABSTRACT

Disclosed is a transalkylation process for making an aromatic material between a light aromatic material and a heavier aromatic material in the presence of hydrogen and a transalkylation catalyst comprising a hydrogenation component and a transalkylation component. The process comprises conducting the transalkylation reaction under conditions conducive to reducing the amount of cyclic compounds in the transalkylation reaction mixture in the beginning phase of the operation that is different from the conditions after the beginning phase. The invention is useful, e.g., in transalkylation between toluene and C9+ aromatic feed materials to produce xylenes and/or benzene.

18 Claims, No Drawings

TRANSALKYLATION PROCESS

CROSS REFERENCE TO RELATED APPLICATIONS

This application claims priority to and the benefit of U.S. Provisional Application No. 62/094,300, filed Dec. 19, 2014 which is incorporated herein by reference in its entirety.

TECHNICAL FIELD

This invention relates to a transalkylation process for making an aromatic material. In particular, the present invention relates to a transalkylation process between benzene/toluene and heavier aromatic materials. The present invention is useful, e.g., in making xylenes and/or benzene from toluene and aromatic materials comprising nine or more carbon atoms.

BACKGROUND

A source of benzene and xylene is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a six carbon (C6) to eight carbon (C8) fraction is separated from the reformate and extracted with a solvent selective for aromatics or aliphatics to produce a mixture of aromatic materials that is relatively free of aliphatics. This mixture of aromatic materials usually contains benzene, toluene and xylenes (BTX), along with ethylbenzene.

Refineries have also focused on the production of benzene and xylene by transalkylation of an aromatic having nine or more carbons (C9+A) and toluene over noble metal-containing zeolite catalysts. During the transalkylation of C9+A and toluene to high value petrochemical products, such as benzene and xylene, over catalysts containing noble metals, by-products, such as saturated materials, are typically produced in the process. These by-products can boil in the same temperature range as the desired aromatic products, making separation of the desired products at high purity levels difficult. For example, a commercial benzene product may need a purity of 99.85 wt % or higher. However, initial benzene purity after distillation of a transalkylation reaction product is typically only 99.2% to 99.5% due to the presence of coboilers, such as methylcyclopentane, cyclohexane, 2,3-dimethylpentane, dimethylcyclopentane and 3-methylhexane. Therefore, an additional extraction step is usually required to further improve benzene product purity to the desired level.

One solution to the problem of the production of benzene co-boilers during the transalkylation of heavy aromatics is disclosed in U.S. Pat. No. 5,942,651 and involves the steps of contacting a feed comprising C9+A materials and toluene under transalkylation reaction conditions with a first catalyst composition comprising a zeolite having a constraint index ranging from 0.5 to 3, such as ZSM-12, and a hydrogenation component. The effluent resulting from the first contacting step is then contacted with a second catalyst composition which comprises a zeolite having a constraint index ranging from 3 to 12, such as ZSM-5, and which may be in a separate bed or a separate reactor from the first catalyst composition to produce a transalkylation reaction product comprising benzene and xylene. A benzene to product having a purity of at least 99.85% may be obtained by distilling the benzene from the transalkylation reaction product, without the need for an additional extraction step. According to the '651 patent, the second catalyst composition comprises up to 20 wt % of the total weight of the first and second catalyst compositions.

U.S. Pat. No. 5,905,051 discloses a process for converting a hydrocarbon stream such as, for example, a C9+A materials to C6 to C8 aromatic hydrocarbons, such as xylenes, by contacting the stream with a catalyst system comprising a first catalyst composition and a second catalyst composition, wherein said catalyst compositions are present in separate stages and are not physically mixed or blended and wherein said first catalyst composition is a metal-promoted, alumina- or silica-bound zeolite beta, and said second catalyst composition is ZSM-5 having incorporated therein an activity promoter selected from the group consisting of silicon, phosphorus, sulfur, and combinations thereof. According to the '051 patent, the use of the separate catalytic stages improves the conversion of C9+A materials and naphthalenes to xylenes and decreases the amount of undesirable ethylbenzene in the product.

U.S. Pat. No. 5,030,787 discloses an improved disproportionation/transalkylation process. The improved process of this invention is conducted such that transalkylation of a C9+A feedstock, or disproportionation of a feedstock containing toluene and C9+A(s), is carried out in the vapor-phase by containing said feedstock in a reaction zone with a catalyst comprising a zeolite possessing a Constraint Index, as defined below, of from 1 to about 3 and preferably which has been hydrogen, hydrogen precursor and/or non-noble Group VIII metal exchanged, thermally treated and/or hydrothermally treated, under conditions effective to convert such feedstock to a product containing substantial quantities of C6-C8 aromatic materials, e.g., benzene and xylene(s), especially the latter. The product effluent is separated and distilled to remove the desired products. If desired, any unreacted material(s), e.g., toluene and/or C9+ material, can be recycled.

U.S. Pat. No. 5,030,787 discloses a transalkylation process to convert a heavy aromatics feed to lighter aromatics products, such as benzene, toluene and xylenes by contacting a C9+A fraction and benzene and/or toluene over a catalyst comprising a zeolite, such as ZSM-12, and a hydrogenation component, preferably platinum. The catalyst, with hydrogenation component, is treated to reduce aromatics loss. Treatment includes exposure to steam and/or sulfur after incorporation of the hydrogenation component. For additional stability and aromatics retention, the steamed and/or sulfur treated catalyst is sulfided by cofeeding a source of sulfur. In a further embodiment of the invention, a low hydrogen partial pressure is employed to retain aromatics.

U.S. Pat. No. 7,663,010 discloses a catalyst system adapted for transalkylation of a C9+ aromatic material (C9+A) feedstock with a C6 aromatic material (C6A) and/or C7 aromatic material (C7A) feedstock, comprising: (a) a first catalyst comprising a first molecular sieve having a Constraint Index in the range of 3-12 and 0.01 to 5 wt % of at least one source of a first metal element of Groups 6-10; and (b) a second catalyst comprising a second molecular sieve having a Constraint Index less than 3 and 0 to 5 wt % of at least one source of a second metal element of Groups 6-10, wherein the weight ratio of the first catalyst over the second catalyst is in the range of 5:95 to 75:25, and wherein the first catalyst is located in front of the second catalyst when they are brought into contact with the C9+A feedstock and the C6A and/or C7A feedstock in the presence of hydrogen. According to this patent, the catalyst system has improved aging rates and enables transalkylation at a high throughput.

SUMMARY

It has been found that in transalkylation reaction processes using a catalyst comprising a transalkylation component and a hydrogenation metal component in the presence of hydrogen, hydrogenation of aromatic rings can occur resulting in the production of non-negligible amount of alicyclic compounds. It is highly desirable the amount of such alicyclic compounds is reduced in the transalkylation product mixture. It has been found that by conducting the transalkylation reaction process under a set of conditions in the beginning phase of the reaction process different from the set of conditions in the subsequent operation, one can significantly reduce the overall formation of alicyclic compounds in the process.

Accordingly, the present invention provides a transalkylation process comprising conducting a transalkylation reaction between a C6A material and/or C7A material hydrocarbon with a nine carbon aromatic material (C9A) and/or ten carbon aromatic material (C10A) hydrocarbon in a transalkylation reactor in the presence of a transalkylation catalyst comprising a transalkylation component and a hydrogenation metal component under transalkylation conditions, the process comprising: (i) conducting the transalkylation reaction under a first set of transalkylation conditions in the beginning phase of the operation cycle; and (ii) conducting the transalkylation reaction under a second set of transalkylation conditions differing from the first set of transalkylation conditions after the beginning phase of the operation cycle; such that the amount of alicyclic compounds in the transalkylation product mixture in the beginning phase is reduced compared to conducting the transalkylation reaction under the second set of transalkylation conditions in the beginning phase.

DETAILED DESCRIPTION

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used. Likewise, "a C9+ component" should be interpreted to include one, two or more C9+ components, unless specified or indicated by the context to mean only one specific C9+ component.

As used herein, the generic term "xylene," either in singular or plural form, shall collectively mean any mixture of two or three of para-xylene, meta-xylene, and ortho-xylene at any proportion thereof. The term "mixed xylenes" means a combination of all three isomers of xylene.

As used herein, the term "rich" when used in phrases such as "X-rich" or "rich in X" means, with respect to an outgoing stream obtained from a device, that the stream comprises material X at a concentration higher than in the feed material fed to the same device from which the stream is derived.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, e.g., the concentrations of the various components of the first feed are expressed based on the total weight of the first feed. All ranges expressed herein should include both end points as two specific embodiments unless specified or indicated to the contrary.

As used herein, the term "alicyclic compound" means a compound that comprises a carbon ring that is non-aromatic. An alicyclic compound can be saturated or unsaturated. Thus, examples of alicyclic compounds include, but are not limited to: cyclopentane, methylcyclopentane, ethylcyclopentane, dimethylcyclopentanes, trimethylcyclopentanes, methylethylcyclopentanes, propylcyclopentanes, cyclohexane, methylcyclohexane, dimethylcyclohexanes, trimethylcyclohexanes, methylethylcyclohexanes, propylcyclohexanes, cycloheptane, methylcycloheptane, dimethylcycloheptanes, ethylcycloheptane, methylethylcycloheptanes, trimethylcycloheptanes, cyclopentene, alkyl substituted cyclopentenes, cyclohexene, alkyl substituted cyclohexenes, cyclohexylbenzene, substituted cyclohexylbenzenes, and the like. A saturated alicyclic compound means a compound that comprises a carbon ring, wherein the ring is saturated and therefore non-aromatic. Non-limiting examples of saturated alicyclic compounds include: cyclopentane, alkyl-substituted cyclopentanes, cyclohexane, and alkyl-substituted cyclohexanes, and the like. Alicyclic compounds can be produced by the hydrogenation of an aromatic compound or another alicyclic compound.

As used herein, the term "substantially free" means less than 1 wt %, preferably less than 0.1 wt %. For example, that a product is substantially free of olefinic components means the product has less than 1 wt %, preferably less than 0.1 wt % olefinic components based on the total weight of the product.

The term "aromatic" as used herein is to be understood in accordance with its art-recognized scope which includes alkyl substituted and unsubstituted mono- and polynuclear compounds.

The term "Cn" wherein n is a positive integer, e.g., 1, 2, 3, 4, 5, 6, 7, 8, 9, 10, 11, 12, as used herein, means organic compound(s) having n number of carbon atom(s) per molecule. The term "Cn+" wherein n is a positive integer, e.g., 1, 2, 3, 4, 5, 6, 7, 8, 9, 10, 11, 12, as used herein, means organic compound(s) having at least n number of carbon atom(s) per molecule. The term "Cn−" wherein n is a positive integer, e.g., 1, 2, 3, 4, 5, 6, 7, 8, 9, 10, 11, 12, as used herein, means organic compound(s) having no more than n number of carbon atom(s) per molecule. The terms "CnA material", "Cn+A material," and "Cn−A material" mean Cn aromatic compound(s)-containing material, Cn+ aromatic compound(s)-containing material, and Cn− aromatic compound(s)-containing material, respectively. Thus, C6A includes benzene; C7A includes toluene; C8A includes xylenes and ethylbenzene; C9A includes trimethylbenzenes, ethylmethylbenzenes, and propylbenzenes; and C10A includes tetramethylbenzenes, diethylbenzenes, ethyldimethylbenzenes, methylpropylbenzenes, butylbenzenes, and the like. As used herein, "C6A/C7A" means a material that may comprise only C6A, only C7A, or a combination or mixture of C6A and C7A. Thus, a C6A/C7A feed may comprise only benzene, only toluene, or a mixture of benzene and toluene, as the case may be. Likewise, "C9A/C10A" means a material that may comprise only C9A, only C10A, or a combination or mixture comprising both C9A and C10A.

The xylene yield, as used herein, is calculated by dividing the total weight of the xylene isomers (para-, meta-, and ortho-xylenes) by the total weight of the product stream. The total weight of the xylene isomers can be calculated by multiplying the weight percentage of the xylene isomers, as determined by gas chromatography, by the total weight of the product stream.

The ring-loss ("RL"), as used herein, is calculated by the following formula:

$$RL = \left(1 - \frac{\text{total moles of aromatic rings in products}}{\text{total moles of aromatic rings in feed}}\right) \times 100\%.$$

For the purpose of calculating the total moles of aromatic rings in a compound, each benzene (or phenol) ring is counted as one aromatic ring. Thus, each mole of benzene, toluene, xylene, ethylbenzene, trimethylbenzenes, has one mole of aromatic ring; and each mole of biphenyl has two moles of aromatic rings.

The methyl over aromatic ring ratio is calculated by dividing the total moles of methyl group attached to an aromatic ring in an aromatic feedstock over the total moles of single aromatic ring in the same aromatic feedstock.

The term "ethyl-aromatic compounds" means aromatic compounds having an ethyl group attached to the aromatic ring. The term "propyl-aromatic compounds" means aromatic compounds having a propyl group attached to the aromatic ring.

The ethyl content of the C9+A feedstock is calculated by multiplying the molecular weight of $C_2H_5-$ by the total mole fraction of aromatics having an ethyl group, where single ethyl substituted aromatics, e.g., 1,4-ethyltoluene are counted once, and di-substituted aromatic rings, e.g., 1,2-diethylbenzene, are counted twice.

The propyl content of the C9+A feedstock is calculated by multiplying the molecular weight of $C_3H_7-$ by the total mole fraction of aromatics having a propyl group, where single propyl substituted aromatics, e.g. n-propylbenzene are counted once, and di-substituted aromatic rings, e.g., 1,4-dipropylbenzene, are counted twice.

Weight of molecular sieve, weight of binder, weight of catalyst composition, weight ratio of molecular sieve over catalyst composition, weight ratio of the first catalyst over the second catalyst and weight ratio of binder over catalyst composition are calculated based on calcined weight (at 510° C. in air for 24 hours), i.e., the weight of the molecular sieve, the binder, and the catalyst composition are calculated based on the weight of the molecular sieve, the binder, and the catalyst composition after being calcined at 510° C. in air for twenty-four hours.

The "beginning phase" of a transalkylation process as used herein means the initial period of the transalkylation process after a fresh catalyst is exposed to the transalkylation reaction conditions. The beginning phase can range from several hours to several months, e.g., 2 hours to 6 months. Preferably, the beginning phase ranges from 8 hours to 180 days. More preferably, the beginning phase ranges from 10 hours to 120 days, or from 12 hours to 90 days, or from 18 hours to 60 days, or from 24 hours to 30 days, or from 36 hours to 15 days, or from 48 hours to 7 days.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

Improving catalytic activity and stability are challenges for most of the catalytic transalkylation processes. High activity catalyst normally requires less catalyst and/or less severe reaction conditions to manufacture the same amount of product, which means lower cost for production and higher production efficiency. As the catalyst ages with increasing time on stream, higher temperatures are normally required to maintain constant conversion. When the maximum reactor temperature is reached, the catalyst needs to be replaced or regenerated. Depending on the feed composition, the cycle length varies from a few months to as long as a few years for a transalkylation catalyst. A catalyst having high stability normally requires less frequent regeneration or change-out and will operate for a long time on stream, which translates to lower cost for production and high production efficiency.

The aging rate of catalysts used for the transalkylation of heavy aromatics is normally dependent on the nature of the feed composition. The higher the ratio of C9+A to C6A and C7A, the greater the aging rate. In addition, the aging rate usually increases with an increasing concentration of material having C10+A, which can be formed as by-products of the transalkylation process. There are many chemical reactions that can lead to the formation of these heavier compounds, for example:

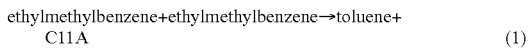
$$\text{ethylmethylbenzene} + \text{ethylmethylbenzene} \rightarrow \text{toluene} + C11A \quad (1)$$

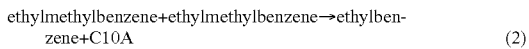
$$\text{ethylmethylbenzene} + \text{ethylmethylbenzene} \rightarrow \text{ethylbenzene} + C10A \quad (2)$$

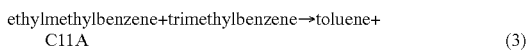
$$\text{ethylmethylbenzene} + \text{trimethylbenzene} \rightarrow \text{toluene} + C11A \quad (3)$$

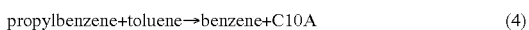
$$\text{propylbenzene} + \text{toluene} \rightarrow \text{benzene} + C10A \quad (4)$$

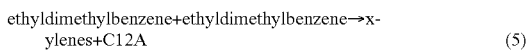
$$\text{ethyldimethylbenzene} + \text{ethyldimethylbenzene} \rightarrow \text{xylenes} + C12A \quad (5)$$

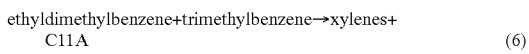
$$\text{ethyldimethylbenzene} + \text{trimethylbenzene} \rightarrow \text{xylenes} + C11A \quad (6)$$

These heavy C10+A compounds may be precursors for the formation of coke which reduces catalyst activity. Therefore, a catalyst that minimizes the production of C10+A compounds is highly desirable. One common feature of these reactions producing heavy aromatics is that most of them contain at least one reactant having an alkyl substituent with two or more carbon atoms, for example, an ethyl group or a propyl group. These molecules normally comprise a significant fraction of the feed to a transalkylation unit. Sometimes, ethyl-methylbenzenes and ethyldimethylbenzenes can comprise up to one third of the C9+ feed to the transalkylation unit. It has now been discovered that minimizing the reactions of these ethyl and propyl aromatics improves catalytic activity and/or aging rate.

In order to minimize C10+A formation, it is preferable to dealkylate the ethyl and propyl groups from the aromatic molecules, and saturate the resulting olefin to prevent realkylation onto an aromatic ring. By dealkylating the ethyl and/or propyl groups in the feedstock, the formation of heavier aromatics, i.e., C10+A, can be minimized, therefore reducing the catalyst aging rate. Thus, using a catalyst system comprising a first catalyst that favors dealkylation over transalkylation reactions and a second catalyst that favors transalkylation over dealkylation reactions and the feedstock feeding to the first catalyst prior to the second catalyst can be advantageous.

In U.S. Pat. No. 7,330,010, a catalyst system for the transalkylation of C9+A with C6A and C7A is disclosed. The catalyst system as disclosed therein comprises (a) a first catalyst comprising a molecular sieve having a Constraint Index in the range of 3-12 (e.g., a 10 MR molecular sieve, such as ZSM-5, ZSM-11, ZSM-22, and ZSM-23) and a metal catalyzing the saturation of the olefins formed by the dealkylation reactions and (b) a second catalyst comprising a molecular sieve having a Constraint Index in the range of less than 3 (e.g., a 12 MR molecular sieve, such as ZSM-12, MOR, zeolite beta, MCM-22 family molecular sieve) and optionally a metal which may be the same or different to the metal on the first catalyst. According to this patent, a process using this catalyst system allows for processing of heavy aromatic feed at high space velocities (high catalytic activity), which provides a significant advantage for a higher throughput transalkylation process and low aging rates for the catalyst system, thereby extending cycle lengths.

U.S. Pat. No. 7,663,010 describes a process for converting a feed comprising C9+A hydrocarbons, hydrogen, and C6A/C7A hydrocarbons to produce a product containing xylenes. The process involves contacting a C9+A feedstock, hydrogen and a C6A/C7A feedstock with a first catalyst under first conditions and afterwards with a second catalyst under second conditions, resulting in a product substantially free of olefinic components and reduced concentrations of ethyl-aromatic compounds and propyl-aromatic compounds.

The hydrogenation-metal contained in such transalkylation catalyst systems, while promoting hydrogenation of olefins produced during the transalkylation process and thereby suppressing the formation of C10+, also promotes the hydrogenation of aromatic rings such as benzene rings, leading to loss of aromaticity in the products. Byproducts as a result of the ring-loss hydrogenation reactions include, but are not limited to, cyclohexane, methylcyclopentane, methylcyclohexane, 1,2-dimethylcyclopentane, 1,3-dimethylcyclopentane, 1,2-dimethylcyclohexane, 1,3-dimethylcyclohexane, and 1,4-dimethylcyclohexane, and the like. Many of these alicyclic compounds have boiling points similar to benzene, therefore are very difficult to separate from benzene by conventional distillation. For transalkylation processes intended for producing benzene, these alicyclic compounds can become major contaminants in the benzene product. Therefore, there is a need to reduce the formation of such alicyclic compounds in the transalkylation process.

We have found that during the beginning phase of the transalkylation reaction cycle, when the hydrogenation metal present in the catalyst is substantially fresh, it is most active in promoting the hydrogenation of aromatic rings. As the operation progresses, coke materials tend to form and deposit on the surface of the catalyst, leading to the significant decrease of aromatic ring hydrogenation activity of the metal. Nonetheless, the olefin hydrogenation activity of the hydrogenation metal in the transalkylation catalyst remains sufficient after the beginning phase.

We have also found that during the transalkylation operations, compounds with saturated aliphatic rings, such as those produced as a result of hydrogenation of aromatic rings, may undergo cracking reactions under the transalkylation reaction conditions in the presence of the transalkylation catalyst simultaneously to form paraffins, thereby reducing the total amount of saturated ring compounds in the product.

We found that by adjusting the transalkylation reaction conditions (including but not limited to feed compositions, temperature, hydrogen partial pressure, and the like) at the beginning phase of the transalkylation reaction, such that exothermic reactions are favored, the total amount of alicyclic compounds formed in the transalkylation process can be reduced appreciably. Without intending to be bound by a particular theory, we believe this is because at least one of the following occurred: (i) formation of alicyclic compounds decreased; (ii) cracking of alicyclic compounds, especially C5-C8 alicyclic compounds, increased; and (iii) overall formation of alicyclic compounds is offset by cracking of alicyclic compounds. At the end of the beginning phase, the hydrogenation metal in the transalkylation catalyst would have been exposed to sufficient amount of coke material, and therefore its ring-loss catalytic activity would have decreased to a tolerable level. Normal transalkylation operation can then be conducted without substantial production of alicyclic compounds.

Catalyst Composition

The catalyst used in the process of the present invention comprises at least one transalkylation component and at least one hydrogenation component, and optionally at least one inorganic binder.

The transalkylation component can be a solid acid such as a molecular sieve, e.g., m a aluminosilicate molecular sieve selected from the following framework types: CHA, EMT, ERI, EUO, FAU, FER, HEU, KFI, LEV, LTA, MAZ, MEI, MEL, MFI, MTT, MTW, MWW, TON, and mixtures and combinations thereof.

The hydrogenation component can be a metal selected from nickel, rhodium, palladium, ruthenium, rhenium, osmium, iridium, platinum, and mixtures and combinations thereof.

The inorganic binder can be selected from oxides of metals of Groups 1, 2, 3, 5, 6, 14, and 15, and mixtures, combinations and compounds thereof. Non-limiting examples of the inorganic binder can be: alumina, silica, zirconia, titania, mixtures and combinations thereof, and their compounds with one or more of oxides of alkali metals, oxides of alkaline earth metals, $P_2O_5$, and the like.

The catalyst used in the process of the present invention may be a catalyst system comprising two or more catalysts. For example, a preferred catalyst system useful in the process of the present invention comprises: (a) a first catalyst comprising a first molecular sieve having 0.01 to 5 wt % of at least one source of a first metal element of Groups 6-10 and a Constraint Index in the range of 3-12; and (b) a second catalyst comprising a second molecular sieve having 0 to 5 wt % of at least one source of a second metal element of Groups 6-10 and a Constraint Index less than 3 and, wherein the weight ratio of the first catalyst over the second catalyst is in the range of 5:95 to 75:25 and wherein the first catalyst is located in front of the second catalyst when they are brought into contacting with the C9+A feedstock and the C6A/C7A feedstock in the present of hydrogen.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the constraint index, and aluminosilicates of this kind usually have pores of small size, e.g., less than 5 Angstroms. On the other hand, aluminosilicates which provide relatively free access to the internal aluminosilicate structure have a low value for the constraint index, and usually pores of large size. The method by which constraint index is determined is described fully in U.S. Pat. No. 4,016,218, which is incorporated herein by reference for the details of the method.

A molecular sieve having a Constraint Index of 3-12 (as defined in U.S. Pat. No. 4,016,218), includes ZSM-5, ZSM-11, ZSM-22, ZSM-23, ZSM-35, ZSM-48, ZSM-57, and ZSM-58. ZSM-5 is described in detail in U.S. Pat. Nos. 3,702,886 and Re. 29,948. ZSM-11 is described in detail in U.S. Pat. No. 3,709,979. ZSM-22 is described in U.S. Pat. Nos. 4,556,477 and 5,336,478. ZSM-23 is described in U.S. Pat. No. 4,076,842. ZSM-35 is described in U.S. Pat. No. 4,016,245. ZSM-48 is more particularly described in U.S. Pat. Nos. 4,234,231 and 4,375,573. ZSM-57 is described in U.S. Pat. No. 4,873,067. ZSM-58 is described in U.S. Pat. No. 4,698,217. The entire contents of all the above patent specifications are incorporated herein by reference.

A molecular sieve having a Constraint Index of less than 3 (as defined in U.S. Pat. No. 4,016,218), includes zeolite beta, zeolite Y, Ultrastable Y (USY), Dealuminized Y (Deal Y), mordenite, ZSM-3, ZSM-4, ZSM-12, ZSM-18, NU-87, and ZSM-20. Zeolite ZSM-4 is described in U.S. Pat. No. 3,923,636. Zeolite ZSM-12 is described in U.S. Pat. No. 3,832,449. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

In one embodiment, the first molecular sieve is a ten member ring molecular sieve and the second molecular sieve is a twelve member ring molecular sieve. Examples of ten member ring molecular sieve are ZSM-5, ZSM-11, ZSM-22, ZSM-23, ZSM-35, ZSM-48, ZSM-57, and ZSM-58. Examples of twelve member ring molecular sieve are zeolite beta, zeolite Y, Ultrastable Y (USY), Dealuminized Y (Deal Y), mordenite, ZSM-3, ZSM-4, ZSM-12, ZSM-18, NU-87, and ZSM-20.

With regard to the molecular sieve having a Constraint Index of less than 3, ZSM-12 is more particularly described in U.S. Pat. No. 3,832,449. Mordenite occurs naturally but may also be used in one of its synthetic forms, such as TEA-mordenite (i.e., synthetic mordenite prepared from a reaction mixture comprising a tetraethylammonium directing agent), which is disclosed in U.S. Pat. Nos. 3,766,093 and 3,894,104. Examples of suitable porous crystalline inorganic oxide materials having the defined X-ray diffraction pattern include MCM-22, PSH-3, SSZ-25, MCM-36, MCM-49 or MCM-56. MCM-22 is described in U.S. Pat. No. 4,954,325, PSH-3 is described in U.S. Pat. No. 4,439,409, SSZ-25 is described in U.S. Pat. No. 4,826,667, MCM-36 is described in U.S. Pat. No. 5,250,277, MCM-49 is described in U.S. Pat. No. 5,236,575, and MCM-56 is described in U.S. Pat. No. 5,362,697. The entire contents of each of the aforementioned patents are incorporated herein by reference.

Typically, the first catalyst comprises at least 1 wt %, preferably at least 10 wt %, more preferably at least 50 wt %, and most preferably at least 65 wt %, of the first molecular sieve. The second catalyst comprises at least 1 wt %, preferably at least 10 wt %, more preferably at least 50 wt %, and most preferably at least 65 wt %, of the second molecular sieve.

The catalyst system has a weight ratio of the first catalyst over the second catalyst in the range of 5:95 to 75:25, preferably in the range of 10:90 to 60:40, and more preferably in the range of 20:80 to 50:50.

In some embodiments, the first molecular sieve has an Alpha value of at least 150, such as at least 300. In other embodiments, the first molecular sieve has an Alpha value in the range of 100-1500, preferably in the range of 300-600.

Where the first molecular sieve is ZSM-5, the ZSM-5 can have a composition involving the molar ratio of $YO_2$ over $X_2O_3$ of n, wherein X is a trivalent element, such as aluminum, boron, iron, indium and/or gallium, preferably aluminum; Y is a tetravalent element, such as silicon, tin and/or germanium, preferably silicon; and n is less than 1000, such as from 10 to less than 100. The ZSM-5 may further be selected so as to have an average crystal size of less than 0.1 micron, such as about 0.05 micron, and a Diffusion Parameter, $D/r^2$, for mesitylene of at least $1000\times10^{-6}$ $sec^{-1}$, such as at least $2000\times10^{-6}$ $sec^{-1}$, when measured at a temperature of 100° C. and a mesitylene pressure of 2 torr.

In a preferred embodiment, the first molecular sieve is ZSM-5 and the second molecular sieve is ZSM-12.

Where the second molecular sieve is ZSM-12, the ZSM-12 can have a composition involving the molar $YO_2$ over $X_2O_3$=n, wherein X is a trivalent element, such as aluminum, boron, iron, indium and/or gallium, preferably aluminum; Y is a tetravalent element, such as silicon, tin and/or germanium, preferably silicon; and n is less than 500, such as from 50 to less than 300. The ZSM-12 may further be selected so as to have an average crystal size of less than 0.1 micron, such as about 0.05 micron, and a Diffusion Parameter, $D/r^2$, for mesitylene of at least $1000\times10^{-6}$ $sec^{-1}$, such as at least $2000\times10^{-6}$ $sec^{-1}$, when measured at a temperature of 100° C. and a mesitylene pressure of 2 torr.

As used herein, the Diffusion Parameter of a particular porous crystalline material is defined as $D/r^2\times10^6$, wherein D is the diffusion coefficient ($cm^2$/sec) and r is the crystal radius (cm). The required diffusion parameters can be derived from sorption measurements provided the assumption is made that the plane sheet model describes the diffusion process. Thus, for a given sorbate loading Q, the value Q/Q', where Q' is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

In some embodiments, the second molecular sieve has an Alpha value of at least 20, such as at least 30. In other embodiments, the second molecular sieve has an Alpha value in the range of 20-500, preferably in the range of 20-100, alternatively in the range of 40-100 or 30-100.

The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

It may be desirable to incorporate each molecular sieve in the catalyst composition with another material that is resistant to the temperatures and other conditions employed in the transalkylation process of the disclosure. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

Use of a material in conjunction with each molecular sieve, i.e., combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, naturally occurring clays, e.g., bentonite and kaolin, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with each molecular sieve as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, each molecular sieve can be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

Each molecular sieve is usually admixed with the binder or matrix material so that the final catalyst composition contains the binder or matrix material in an amount ranging from 5 to 95 wt %, and typically from 10 to 60 wt %.

The first catalyst comprises 0.01 to 5 wt %, preferably 0.1 to 2 wt %, more preferably 0.1 to 1 wt %, of a first metal element of Groups 6-10. The second catalyst comprises 0 to 5 wt %, preferably 0.01 to 2 wt %, more preferably 0.01 to 1 wt %, of a second metal element of Groups 6-10. The first metal element and the second metal element may be at least one hydrogenation component, such as tungsten, vanadium, molybdenum, rhenium, chromium, manganese, a metal selected from Groups 6-10 of the Periodic Table of the Elements, or mixtures thereof. Specific examples of useful metals are iron, ruthenium, rhenium, osmium, nickel, cobalt, rhodium, iridium, and noble metals such as platinum or palladium. Preferably, the hydrogenation component is palladium, platinum, rhenium or combinations thereof.

The amount of the hydrogenation component is selected according to a balance between hydrogenation activity and catalytic functionality. Less of the hydrogenation component is required when the most active metals such as platinum are used as compared to palladium, which does not possess such strong hydrogenation activity. Generally, the catalyst composition contains less than 5 wt % of the hydrogenation component and typically from 0.01 wt % to 2 wt % of the component.

The hydrogenation component can be incorporated into the catalyst composition by co-crystallization, exchanged into the composition to the extent a Group 13 element, e.g., aluminum, is in the molecular sieve structure, impregnated therein, or mixed with the molecular sieve and binder. Such component can be impregnated in or on the molecular sieve, for example in the case of platinum, by treating the molecular sieve with a solution containing a platinum metal-containing ion. Suitable platinum compounds for impregnating the catalyst with platinum include chloroplatinic acid, platinous chloride and various compounds containing the platinum ammine complex, such as $Pt(NH_3)_4Cl_2\cdot H_2O$.

Alternatively, a compound of the hydrogenation component may be added to the molecular sieve when it is being composited with a binder, or after the molecular sieve and binder have been formed into particles by extrusion or pelletizing.

After treatment with the hydrogenation component, the molecular sieve is usually dried by heating at a temperature of 65° C. to 160° C., typically 110° C. to 143° C., for at least 1 minute and generally not longer than 24 hours, at an absolute internal pressure in a range from 100 kPa to 200 kPa. Thereafter, the molecular sieve may be calcined in a stream of dry gas, such as air or nitrogen, at temperatures of from 260° C. to 650° C. for 1 to 20 hours. Calcination is typically conducted at an absolute internal pressures ranging from 100 kPa to 300 kPa.

Prior to use, steam treatment of the catalyst composition may be employed to minimize the aromatic hydrogenation activity of the catalyst composition. In the steaming process, the catalyst composition is usually contacted with from 5 to 100% steam, at a temperature of at least 260° to 650° C. for at least one hour, specifically 1 to 20 hours, at a pressure of 100 to 2590 kPa-a.

In addition, prior to contacting the catalyst composition with the hydrocarbon feed, the hydrogenation component can be sulfided. This is conveniently accomplished by contacting the catalyst with a source of sulfur, such as hydrogen sulfide, at a temperature ranging from about 320° C. to 480° C. The source of sulfur can be contacted with the catalyst via a carrier gas, such as hydrogen or nitrogen. Sulfiding per se is known and sulfiding of the hydrogenation component can be accomplished without more than routine experimentation by one of ordinary skill in the art in possession of the present disclosure.

Apparatus

In some embodiments, this disclosure relates to apparatus adapted for transalkylation of a C9+ feedstock comprising:

(a) a reactor containing a first catalyst having a first molecular sieve having a Constraint Index in the range of 3-12 and followed by a second catalyst having a second molecular sieve having a Constraint Index less than 3; and (b) means for contacting a C9+ feedstock and a C6A/C7A feedstock to the first catalyst under first conditions and then to the second catalyst under second conditions.

In one aspect, the first conditions are the same as the second conditions. In another aspect, the first catalyst is loaded in a first reaction zone of the reactor and the second catalyst is loaded in a second reaction zone of the reactor.

In other embodiments, this disclosure relates to apparatus adapted for transalkylation a C9+ feedstock comprising:

(a) a first reactor containing a first catalyst having a first molecular sieve having a Constraint Index in the range of 3-12 and followed by a second reactor containing a second catalyst having a second molecular sieve having a Constraint Index less than 3; and (b) means for contacting a C9+ feedstock and a C6A/C7A feedstock to the first catalyst under first conditions and then to the second catalyst under second conditions.

In the apparatus of the disclosure, the first and second catalysts may be loaded in the same reactor, or may be loaded in two separate reactors. In all situations, the first catalyst is not mixed with the second catalyst and the hydrocarbon feedstocks and hydrogen are contacting with the first catalyst prior to contacting the second catalyst. In some embodiments, the first catalyst may be separated from the second catalyst by space or by inert materials, such as, alumina balls or sand. The means for contacting a C9+ feedstock and a C6A/C7A feedstock to the first catalyst under first conditions and then to the second catalyst under second conditions include:

(a) load the first catalyst on the top of the second catalyst when the hydrocarbon feedstocks are flowing top-down;

(b) load the second catalyst on the top of the first catalyst when the hydrocarbon feedstocks are flowing bottom-up;

(c) load the first catalyst in the inner part of the reactor and the second catalyst outside of the first catalyst loading when the hydrocarbon feedstocks are flowing inside-out; or (d) load the second catalyst in the inner part of the reactor and the first catalyst outside of the second catalyst loading when the hydrocarbon feedstocks are flowing from outside to inside.

Means for contacting a C9+ feedstock and a C6A/C7A feedstock to the first catalyst under first conditions and then to the second catalyst under second conditions include pipe arrangement, control valves, flow meters, pumps, or any combination thereof. Other means for contacting a C9+ feedstock and a C6A/C7A feedstock to the first catalyst under first conditions and then to the second catalyst under second conditions include pumping or supplying the C9+ feedstock and C6A/C7A feedstock to the catalyst and followed by pumping or supplying the product of the first contacting step to the second catalyst.

Feedstock

The aromatic material feed used in the process of the disclosure comprises one or more aromatic compounds containing at least 9 carbon atoms. Specific C9+A compounds found in a typical feed include mesitylene (1,3,5-trimethylbenzene), durene (1,2,4,5-tetramethylbenzene), hemimellitene (1,2,4-trimethylbenzene), pseudocumene (1,2,4-trimethylbenzene), 1,2-methylethylbenzene, 1,3-methylethylbenzene, 1,4-methylethylbenzene, propyl-substituted benzenes, butyl-substituted benzenes, and dimethylethylbenzenes. Suitable sources of the C9+A are any C9+ fractions from any refinery process that is rich in aromatics. This aromatic fraction contains a substantial proportion of C9+A, e.g., at least 80 wt % C9+A, wherein preferably at least 80 wt %, and more preferably more than 90 wt %, of the hydrocarbons will range from C9 to C12. Typical refinery fractions which may be useful include catalytic reformate, FCC naphtha or TCC naphtha.

The feed to the process of the disclosure may preferably include benzene and/or toluene. In one practical embodiment, the feed to the transalkylation reactor comprises C9+A hydrocarbons and toluene. The feed may also include recycled/unreacted toluene and C9+A feedstock that is obtained by distillation of the effluent product of the transalkylation reaction itself. E.g., toluene or benzene may constitute from c1 wt % to c2 wt % of the entire C6A/C7A feed to the transalkylation reaction, where c1 and c2 can be, independently, 0, 1, 3, 5, 7, 9, 10, 15, 20, 25, 30, 35, 40, 45, 50, 55, 60, 65, 70, 75, 80, 85, 90, 91, 92, 93, 94, 95, 96, 97, 98, 99, 99.5, 99.9, as long as c1<c2.

The mole ratio of the C6A/C7A feed to the C9+A feed into the transalkylation reaction can range from Rm1 to Rm2, where Rm1 and Rm2 can be, independently, 0, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, as long as Rm1<Rm2.

The feedstock may be characterized by the methyl over single aromatic ring molar ratio. In some embodiments, the combined feedstock (the combination of the C9+ and the C6A/C7A feedstocks) has a methyl over single aromatic ring molar ratio in the range of from 0.5 to 4, preferably from 1 to 2.5, more preferably from 1.5 to 2.25. The methyl over single aromatic ring molar ratio may be adjusted by adjusting relative flow rate of the C9+ and the C6A/C7A feedstocks and/or the relative C6A/C7A ratio of the C6A/C7A feedstock.

Even if the feedstock supplied to the transalkylation reaction process is substantially free of benzene and toluene, benzene and toluene may nonetheless be produced in the transalkylation process. Thus, in-situ produced C6A and C7A materials in the transalkylation process can range from c1 mol % to c2 mol % of the total C6A and C7A in the transalkylation process, where c1 and c2 can be, independently, 1, 3, 5, 7, 9, 10, 15, 20, 25, 30, 35, 40, 45, 50, 55, 60, 65, 70, 75, 80, 85, 90, 95, 99, 100, as long as c1<c2. The in-situ produced C6A/C7A material(s) in the transalkylation reaction can further undergo (i) additional transalkylation reactions with the C9+A compounds supplied to the transalkylation process and (ii) hydrogenation reactions with hydrogen to produce alicyclic compounds.

It has been surprisingly found that by reducing the total feed rate of the C6A, C7A, C9A and C10A to the transalkylation process in the beginning phase, one can reduce the formation of alicyclic compounds and ring-loss. Thus, where the total feed rate of the C6A material, the C7A material, the C9A material, and the C10A material under the first set of transalkylation conditions is Rf1 moles/hour, the total feed rate of the C6A material, the C7A material, the C9A material, and the C10A material under the second set of transalkylation conditions is Rf2 moles/hour, it is desired that r1≤Rf1/Rf2≤r2, where r1 and r2 can be, independently, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 0.97, 0.98, as long as r1<r2.

Transalkylation Process

In some embodiments, this disclosure relates to a process for producing xylene comprising:

(a) contacting a C9+A feedstock, hydrogen and a C6A/C7A feedstock with a first catalyst comprising 0.01 to 5 wt %, preferably 0.01 to 1 wt %, of at least one source of a first metal element of Groups 6-10 and a first molecular sieve having a Constraint Index in the range of 3-12 under first conditions to form a first product, wherein the first conditions are selected such that the first product is substantially free of olefinic components and the first product contains at least 50 wt % less ethyl-aromatic compounds and at least 75 wt % less propyl-aromatic compounds than the C9+A feedstock; then (b) contacting at least a portion of the first product with a second catalyst comprising 0 to 5 wt %, preferably 0.01 to 1 wt %, of at least one source of a second metal element of Groups 6-10 and a second molecular sieve having a Constraint Index less than 3 under second conditions, wherein the second conditions are sufficient to transalkylate at least a portion of the C9+A compounds in the C9+A feedstock with at least a portion of the C6A/C7A compounds in the C6A/C7A feedstock to form a second product comprising xylene, wherein the second conditions are selected such that the second product is substantially free of olefinic components and the xylene yield is in the range of 20 to 50 wt %, and wherein the second product contains at least 60 wt %, preferably at least 65 wt %, still more preferably at least 70 wt % less ethyl-aromatic compounds and at least 70 wt %, preferably at least 75 wt %, still more preferably at least 85 wt % less propyl-aromatic compounds than the C9+A feedstock; and (c) recovering the xylene.

In another embodiments, this disclosure relates to a process comprising:

(a) contacting a C9+A feedstock with a first catalyst comprising 0.01 to 5 wt %, preferably 0.01 to 1 wt % of at least one source of a first metal element of Groups 6-10 and a first molecular sieve having a Constraint Index in the range of 3-12 under first conditions to form a first product, wherein the first conditions are selected such that the first product is substantially free of olefinic components and the first product contains at least 50 wt % less ethyl-aromatic compounds and at least 75 wt % less propyl-aromatic compounds than the C9+A feedstock; and then (b) contacting at least a portion of the first product with a second catalyst comprising 0 to 5 wt %, preferably 0.01 to 1 wt %, of at least one source of a second metal element of Groups 6-10 and a second molecular sieve having a Constraint Index less than 3 under second conditions to form a second product, wherein the second conditions are selected such that the second product is substantially free of olefinic components and the xylene yield is in the range of 20 to 50 wt %, and wherein the second product contains at least 60 wt %, preferably at least 65 wt %, still more preferably at least 70 wt % less ethyl-aromatic compounds and at least 70 wt %, preferably at least 75 wt %, still more preferably at least 85 wt % less propyl-aromatic compounds than the C9+A feedstock.

The process can be conducted in any appropriate reactor including a radial flow, fixed bed, continuous down flow or fluid bed reactor. The first conditions and/or the second conditions comprise a temperature in the range of 100 to 1000° C., preferably in the range of 300 to 500° C.; a pressure in the range of 790 to 7000 kPa-a (kilo-Pascal absolute), preferably in the range of 2170 to 3000 kPa-a, a $H_2$:HC molar ratio in the range of 0.01 to 20, preferably in the range of 1-10; a WHSV in the range of 0.01 to 100 $hr^{-1}$, preferably in the range of 1-20. The second conditions comprise a temperature in the range of 100 to 1000° C., a pressure in the range of 790 to 7000 kPa-a, a $H_2$:HC molar ratio in the range of 0.01 to 20, a WHSV in the range of 0.01 to 100 $hr^{-1}$.

The first and/or the second conditions may be same. The first and the second conditions are sufficient to convert the heavy aromatic feed to a product containing more xylene than the combined feedstock.

In some embodiments, the first conditions are selected such that the first product is substantially free of olefinic components and the first product contains at least 50 wt % less, preferably at least 70 wt % less, ethyl-aromatic compounds and at least 75 wt % less, preferably at least 85 wt % less, propyl-aromatic compounds than the C9+A feedstock.

In other embodiments, the second conditions are sufficient to transalkylate at least a portion of the C9+A compounds in the C9+A feedstock with at least a portion of the C6A/C7A compounds in the C6A/C7A feedstock to form a second product comprising xylene, wherein the second conditions are selected such that the second product is substantially free of olefinic components and the xylene yield is in the range of 20 to 50 wt %, and wherein the second product contains at least 70 wt % less, preferably at least 80 wt % less, ethyl-aromatic compounds and at least 85 wt % less, preferably at least 95 wt % less, propyl-aromatic compounds than the at least a portion of the first product.

In some embodiments, where the C9+A feedstock and/or the C6A/C7A feedstock contains paraffinic compounds, the process further comprises a step of contacting the paraffinic compounds in the C9+A feedstock and/or the C6A/C7A feedstock with a third catalyst comprising a third molecular sieve having a Constraint Index in the range of 3-12 under first cracking conditions sufficient to crack at least 50 wt % of the paraffinic compounds.

In some embodiments, where the second product contains paraffinic compounds, the process further comprises a step of contacting the paraffinic compounds in the second product with a fourth catalyst comprising a fourth molecular sieve having a Constraint Index in the range of 3-12 under second cracking conditions sufficient to crack at least 50 wt % of the paraffinic compounds in the second product.

The first cracking conditions and/or the second cracking conditions comprise a temperature in the range of 100 to 1000° C., preferably in the range of 300 to 500° C.; a pressure in the range of 790 to 7000 kPa-a (kilo-Pascal absolute), preferably in the range of 2170 to 3000 kPa-a, a H$_2$:HC molar ratio in the range of 0.01 to 20, preferably in the range of 1-10; a WHSV in the range of 0.01 to 100 hr$^{-1}$, preferably in the range of 1-20. The second conditions comprise a temperature in the range of 100° C. to 1000° C., a pressure in the range of 790 to 7000 kPa-a, preferably in the range of 2170 to 3000 kPa-a; a H$_2$:HC molar ratio in the range of 0.01 to 20, a WHSV in the range of 0.01 to 100 hr$^{-1}$.

In other aspects, the first conditions and the second conditions are selected such that the total ring-loss of the process is in the range of 0 to 3 wt %, preferably in the range of 0.5-1.5 wt %.

In all of the above embodiments of the transalkylation processes, and other transalkylation processes, according to the present invention, a first set of transalkylation reaction conditions is imposed in the beginning phase of the process, and a second set of transalkylation reaction conditions different from the first set of transalkylation conditions is imposed thereafter. Such different sets of conditions would apply to both first conditions and second conditions of embodiments involving multiple catalysts and multiple reaction conditions in the system.

Under the transalkylation conditions, in the presence of hydrogen, some of the aromatic rings, including those in the C9+A compounds, C6A, C7A, and C8A compounds, in-situ produced or fed into the transalkylation process, undergo hydrogenation reactions, producing alicyclic compounds. As discussed above, it is highly desirable to minimize the production of such alicyclic compounds and ring-loss.

It has also been found that by reducing hydrogen partial pressure in the beginning phase of transalkylation process, one can reduce ring-loss in the overall transalkylation process. Thus, where the hydrogen partial pressure under the first set of transalkylation conditions includes a hydrogen partial pressure of PH2a; the second set of transalkylation conditions includes a hydrogen partial pressure of PH2b; it is desired that r1≤PH2a/PH2b≤r2, where r1 and r2 can be, independently, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 0.97, 0.98, as long as r1<r2.

It has also been found that by reducing the total internal pressure in the transalkylation reactor, one can reduce ring-loss in the overall transalkylation process. Thus, where the first set of transalkylation conditions includes a total internal pressure of Pip1; the second set of transalkylation conditions includes a total internal pressure of Pip2; it is desired that r1≤Pip1/Pip2≤r2, where r1 and r2 can be, independently, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 0.97, 0.98, as long as r1<r2.

It has also been found that by reducing the ratio of the weight of toluene to the total weight of C7A, C9A, and C10A materials fed to the transalkylation reactor, one can reduce ring-loss in the overall transalkylation process. Thus, where toluene is fed to the transalkylation reactor, under the first set of transalkylation conditions, the ratio of the weight of toluene to the total weight of the C7A, C9A, and C10A materials fed to the transalkylation reactor is Rt1, and under the second set of transalkylation conditions, the ratio of the weight of toluene to the total weight of the C7A, C9A, and C10A materials fed to the transalkylation reactor is Rt2, it is desired that r1≤Rt1/Rt2≤r2, where r1 and r2 can be, independently, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 0.97, 0.98, as long as r1<r2.

It has also been found that by substantially increasing the ratio of the weight of toluene to the total weight of C7A, C9A, and C10A materials fed to the transalkylation reactor, one can reduce ring-loss in the overall transalkylation process. Thus, where toluene is fed to the transalkylation reactor, under the first set of transalkylation conditions, the ratio of the weight of toluene to the total weight of the C7A, C9A, and C10A materials fed to the transalkylation reactor is Rta, and under the second set of transalkylation conditions, the ratio of the weight of toluene to the total weight of the C7A, C9A, and C10A materials fed to the transalkylation reactor is Rtb, it is desired that r1≤Rta/Rtb≤r2, where r1 and r2 can be, independently, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3/9, as long as r1<r2.

As a result of implementing the present invention, one can significant reduce the production of all alicyclic compounds, and particularly C6 and C7 alicyclic compounds, during the beginning phase of the transalkylation process. Thus, where the total average concentrations of alicyclic compounds in the transalkylation product mixture in the beginning phase is Cac1, expressed as total weight percentage of the alicyclic compounds based on the total weight of the transalkylation product mixture; the total average concentrations of alicyclic compounds in the transalkylation product mixture in the beginning phase would be Cac2 if the transalkylation reaction is conducted under the second set of transalkylation conditions, expressed as total weight percentage of the alicyclic compounds based on the total weight of the transalkylation product mixture, r1≤Cac1/Cac2≤r2, where r1 and r2 can be, independently, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3/9, as long as r1<r2. Where the total average concentrations of C6 and C7 alicyclic compounds in the transalkylation product mixture in the beginning phase is Cac3, expressed as weight percentage of the C6 and C7 alicyclic compounds based on the total weight of the transalkylation product mixture; and the total average concentrations of C6 and C7 alicyclic compounds in the transalkylation product mixture in the beginning phase would be Cac4 if the transalkylation reaction is conducted under the second set of transalkylation conditions, the following can be achieved: r3≤Cac3/Cac4≤r4, where r3 and r4 can be, independently, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3/9, as long as r3<r4.

As a result of implementing the present invention, one can significant reduce the production of all alicyclic compounds, and obtain a transalkylation production mixture featured by an increased benzene purity factor (defined below). Thus, where the transalkylation product mixture has an average benzene purity factor of BPF1 in the beginning phase; the transalkylation product mixture in the beginning phase would have an average benzene purity factor of BPF2 if the transalkylation reaction was conducted under the second set of transalkylation conditions; the following can be achieved: a %≤BPF1−BPF2≤b %, where a and b can be, independently, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.3, 1.4, 1.5, 1.6, 1.7, 1.8, 1.9, 2.0, as long as a<b.

EXAMPLES AND DESCRIPTION ACCORDING TO THE DRAWINGS

The present invention is further illustrated by the following non-limiting examples. In these examples, a catalyst system was prepared in substantially the same manner as in U.S. Pat. No. 7,663,010, the content of which is incorporated herein by reference in its entirety. The catalyst system was then tested in substantially the same manner as in U.S. Pat. No. 7,663,010, with variations of conditions specified in each example below. The product mixtures obtained from the experiments were analyzed using gas chromatography. Concentrations of the various components in the product mixture in weight percentages based on the total weight of the product mixture were calculated based on the gas chromatography analysis data. The benzene purity factor (BPF) of each product mixture was then calculated according to the following formula:

$$BPF = \frac{Cbz}{Cbz + 0.1*Cn6 + 0.7*Cmcp + Cch + 0.6*(Cecp + Cdmcp) + 0.05*Cmch} \times 100\%$$

where:
Cbz is the concentration of benzene;
Cn6 is the concentration of n-hexane;
Cmcp is the concentration of methylcyclopentane;
Cch is the concentration of cyclohexane;
Cecp is the concentration of ethylcyclopentane;
Cdmcp is the concentration of dimethylcyclopentane; and
Cmch is the concentration of methylcyclohexane, all in weight percentages based on the total weight of the product mixture.

The BPF calculated above is an indicator of the purity of benzene obtainable from the product mixture using a distillation tower.

In each example below, two or more experiments were conducted to compare the results and demonstrate the effect of changing one parameter in transalkylation reaction conditions.

Example 1: Effect of Weight Hourly Space Velocity

In this example, in Experiments 1A and 1B, a hydrocarbon feed comprising 45 wt % toluene and 55 wt % of C9+A was fed to the transalkylation reactor. In Experiments 1C and 1D, a hydrocarbon feed comprising 65 wt % toluene and 35 wt % of C9+A was fed to the transalkylation reactor. In Experiment 1A, the weight hourly space velocity (WHSV) of the feed was 3.1. In Experiment 1B, the WHSV was reduced to 2.1 while maintaining all other parameters the same as in Experiment 1A. In Experiment 1C, the weight hourly space velocity (WHSV) of the feed was 5.0. In Experiment 1D, the WHSV was reduced to 3.0 while maintaining all other parameters the same as in Experiment 1C. See TABLE 1 below for the key reaction conditions and the calculated BPFs of the reaction product mixtures.

The data in TABLE 1 show that as a result of WHSV decrease while maintaining all other parameters unchanged, the BPF in the reaction product mixture increased from 99.5% in Experiment 1A to 99.7% in Experiment 1B, and from 99.8% in Experiment 1C to 99.9% in Experiment 1D. These consistent results are surprising in that one might have expected that lower space velocity, or higher residence time, might have favored additional undesirable reactions and hence resulted in lower BPF.

Example 2: Effect of Hydrogen Partial Pressure

In this example, a hydrocarbon feed comprising 65 wt % toluene and 35 wt % of C9+A was fed to the transalkylation reactor. In Experiment 2A, the hydrogen to hydrocarbon molar ratio was 4.0. In Experiment 2B, the hydrogen to hydrocarbon molar ratio was reduced to 2.0. See TABLE 2 below for the key reaction conditions and the calculated BPFs of the reaction product mixtures.

TABLE 2

| Items | Experiment 2A | Experiment 2B |
|---|---|---|
| Toluene/C9 + A weight ratio | 65:35 | 65:35 |
| Total Pressure, Gauge (kPa) | 2274 | 2274 |
| WHSV (hour$^{-1}$) | 3.0 | 3.0 |
| Reactor Inlet Temperature (° C.) | 385 | 385 |
| Hydrogen/hydrocarbon molar ratio | 4.0 | 2.0 |
| BPF (%) | 99.3 | 99.5 |

The data in TABLE 2 show that as a result of the hydrogen to hydrocarbon molar ratio decrease while maintaining all other parameters unchanged, the BPF in the reaction product mixture increased from 99.3% to 99.5%. This result is surprising in that one might have expected that higher hydrogen partial pressure (i.e., higher hydrogen to hydrocarbon molar ratio) might have favored exothermic reactions and hence increased reaction zone temperature in a manner that would allow the non-aromatics cracking component of the catalyst system to be more effective, hence additional undesirable reactions and hence resulted in lower BPF.

Example 3: Effect of Reactor Pressure

In this example, a hydrocarbon feed comprising 45 wt % toluene and 55 wt % of C9+A was fed to the transalkylation reactor. In Experiment 3A, the total reactor gauge pressure was 2227 kPa. In Experiment 3B, the total reactor gauge pressure was increased to 2972 kPa. See TABLE 3 below for the key reaction conditions and the calculated BPFs of the reaction product mixtures.

TABLE 3

| Items | Experiment 3A | Experiment 3B |
|---|---|---|
| Toluene/C9 + A weight ratio | 45:55 | 45:55 |
| Total Pressure, Gauge (kPa) | 2227 | 2972 |
| WHSV (hour$^{-1}$) | 3.0 | 3.0 |
| Reactor Inlet Temperature (° C.) | 393 | 393 |

TABLE 1

| Items | Experiment 1A | Experiment 1B | Experiment 1C | Experiment 1D |
|---|---|---|---|---|
| Toluene/C9 + A weight ratio | 45:55 | 45:55 | 65:35 | 65:35 |
| Total Pressure, Gauge (kPa) | 2220 | 2220 | 2275 | 2275 |
| WHSV (hour$^{-1}$) | 3.1 | 2.1 | 5.0 | 3.0 |
| Reactor Inlet Temperature (° C.) | 382 | 382 | 410 | 410 |
| Hydrogen/hydrocarbon molar ratio | 2.0 | 2.0 | 2.0 | 2.0 |
| BPF (%) | 99.5 | 99.7 | 99.8 | 99.9 |

TABLE 3-continued

| Items | Experiment 3A | Experiment 3B |
|---|---|---|
| Hydrogen/hydrocarbon molar ratio | 2.0 | 2.0 |
| BPF (%) | 99.7 | 99.6 |

The data in TABLE 3 show that as a result of reactor pressure increase while maintaining all other parameters unchanged, the BPF in the reaction product mixture decreased from 99.7% to 99.6%.

Example 4: Effect of Reactor Inlet Temperature

In this example, a hydrocarbon feed comprising 65 wt % toluene and 35 wt % of C9+A was fed to the transalkylation reactor. In Experiment 4A, the reactor inlet temperature was 393° C. In Experiment 4B, the reactor inlet temperature was reduced to 373° C. See TABLE 4 below for the key reaction conditions and the calculated BPFs of the reaction product mixtures.

TABLE 4

| Items | Experiment 4A | Experiment 4B |
|---|---|---|
| Toluene/C9 + A weight ratio | 45:55 | 45:55 |
| Total Pressure, Gauge (kPa) | 2972 | 2972 |
| WHSV (hour$^{-1}$) | 3.0 | 3.0 |
| Reactor Inlet Temperature (° C.) | 393 | 373 |
| Hydrogen/hydrocarbon molar ratio | 2.0 | 2.0 |
| BPF (%) | 99.6 | 98.7 |

The data in TABLE 4 show that as a result of reactor inlet temperature decrease while maintaining all other parameters unchanged, the BPF in the reaction product mixture decreased from 99.6% to 98.7%.

While this example suggests that increasing inlet temperature can increase BPF in the production mixture, it might be undesirable to increase reactor inlet temperature early in the operation cycle, because operating at too high a temperature early in the cycle results in high conversion and hence high gas make, and also because operating at high conversion and high severity will decrease the overall cycle length and cause the need for an early catalyst change-out.

Example 5: Effect of Feed Composition

In this example, in Experiment 5A, a hydrocarbon feed comprising 20 wt % toluene and 80 wt % of C9+A was fed to the transalkylation reactor. In Experiment 5B, a hydrocarbon feed comprising 45 wt % toluene and 55 wt % of C9+A was fed to the transalkylation reactor while maintaining all other parameters the same as in Experiment 1A. In Experiment 5C, a hydrocarbon feed comprising 20 wt % toluene and 80 wt % of C9+A was fed to the transalkylation reactor operating at a different pressure from that in Experiment 5A. In Experiment 5D, a hydrocarbon feed comprising 100 wt % toluene was fed to the transalkylation reactor while maintaining all other parameters the same as in Experiment 5C. See TABLE 5 below for the key reaction conditions and the calculated BPFs of the reaction product mixtures.

TABLE 5

| Items | Experiment 5A | Experiment 5B | Experiment 5C | Experiment 5D |
|---|---|---|---|---|
| Toluene/C9 + A weight ratio | 20:80 | 45:55 | 20:80 | 100:0 |
| Total Pressure, Gauge (kPa) | 2220 | 2220 | 2399 | 2399 |
| WHSV (hour$^{-1}$) | 3.0 | 3.0 | 3.0 | 3.0 |
| Reactor Inlet Temperature (° C.) | 382 | 382 | 382 | 382 |
| Hydrogen/hydrocarbon molar ratio | 2.0 | 2.0 | 2.0 | 2.0 |
| BPF (%) | 99.5 | 99.3 | 99.7 | 99.9 |

The data in TABLE 5 show that as a result of an increase in toluene concentration in the feed from 20 wt % in Experiment 5A to 45 wt % in Experiment 5B, while maintaining all other parameters unchanged, the BPF in the reaction product mixture decreased from 99.5% to 99.3%.

In contrast, as a result of drastic increase in toluene content in the hydrocarbon feed from 20 wt % in Experiment 5C to 100 wt % in Experiment 5D, and all other operating conditions being equal, the BPF increased from 99.7% to 99.9%. This result is surprising in that one might have expected that higher toluene in the feed would result in lower coke deposition on the catalyst and hence higher metal activity, which could have favored additional undesirable reactions and hence resulted in lower BPF. While this expectation was verified by Experiments 5A and 5B, it appears in the case of Experiment 5D, a drastically increased toluene concentration may favor ring saturation reactions which increase overall reactor temperature and hence allow the non-aromatics cracking function of the catalyst to become more effective, yielding a higher a product with higher BPF.

The invention claimed is:

1. A transalkylation process comprising:
   supplying a feedstream to the transalkylation reactor, wherein the feedstream comprises toluene, C9 aromatic material, and C10 aromatic material; and
   conducting a transalkylation reaction with the feedstream in the presence of a transalkylation catalyst under transalkylation conditions to produce a transalkylation reaction product mixture comprising at least one alicyclic compound,
   wherein:
   the transalkylation catalyst comprises a hydrogenation metal component;
   in the first set of transalkylation conditions, the feedstream has a first ratio of the weight of the toluene to the total weight of the toluene, the C9 aromatic material, and the C10 aromatic material;
   in the second set of transalkylation conditions, the feedstream has a second ratio of the weight of the toluene to the total weight of the toluene, the C9 aromatic material, and the C10 aromatic material; and
   the first ratio divided by the second ratio is between 1.5 and 3.0, such that ring-loss is reduced in the transalkylation process compared to a transalkylation process operated under the second set of transalkylation conditions only.

2. The process of claim 1, wherein the at least one alicyclic compound is a saturated alicyclic compound.

3. The process of claim 1, wherein the at least one alicyclic compound is selected from cyclopentane, methylcyclopentane, ethylcyclopentane, dimethylcyclopentanes, trimethylcyclopentanes, methylethylcyclopentanes, propylcyclopentanes, cyclohexane, methylcyclohexane, dimethylcyclohexanes, trimethylcyclohexanes, methylethylcyclohexanes, propylcyclohexanes, cycloheptane, methylcycloheptane, dimethylcycloheptanes, ethylcycloheptane, methylethylcycloheptanes, trimethylcycloheptanes, cyclopentene, alkyl substituted cyclopentenes, cyclohexene, alkyl substituted cyclohexenes, and combinations of two or more thereof.

4. The process of claim 1, wherein the transalkylation conditions favor cracking reactions of C5 to C8 alicyclic compounds to form paraffins during the first set of transalkylation conditions.

5. The process of claim 1, wherein at least a portion of the toluene is generated in situ.

6. The process of claim 1, wherein the transalkylation catalyst further comprises a solid acid.

7. The process of claim 6, wherein the solid acid is an aluminosilicate molecular sieve selected from the following framework types: CHA, EMT, ERI, EUO, FAU, FER, HEU, KFI, LEV, LTA, MAZ, MEI, MEL, MFI, MTT, MTW, MWW, TON, and mixtures and combinations thereof.

8. The process of claim 1, wherein the hydrogenation component comprises at least one of nickel, rhodium, palladium, ruthenium, rhenium, osmium, iridium, and platinum.

9. The process of claim 1, wherein the transalkylation reaction product mixture comprises benzene, para-xylene, meta-xylene, ortho-xylene, and toluene.

10. The process of claim 1, wherein:
the transalkylation reaction is conducted under a first hydrogen partial pressure of PH2a in the first set of transalkylation conditions;
the transalkylation reaction is conducted under a second hydrogen partial pressure of PH2b in the second set of transalkylation conditions; and $PH2a<PH2b$, and $0.10 \leq PH2a/PH2b \leq 0.95$.

11. The process of claim 1, wherein:
the transalkylation reaction is conducted under a first total internal pressure of Pip1 in the first set of transalkylation conditions;
the transalkylation reaction is conducted under a second total internal pressure of Pip2 in the second set of transalkylation conditions; and $Pip1<Pip2$, and $0.10 \leq Pip1/Pip2 \leq 0.95$.

12. The process of claim 1, wherein the transalkylation catalyst comprises a first molecular sieve in a first catalyst bed and a second molecular sieve in a second catalyst bed; and
wherein conducting the transalkylation reaction comprises:
supplying the feedstream to the first molecular sieve to produce a first effluent; and
supplying the first effluent to the second molecular sieve.

13. The process of claim 12, wherein the first molecular sieve comprises ZSM-5 and the second molecular sieve comprises ZSM-12.

14. The process of claim 13, wherein the ZSM-5 has a silica to alumina ratio of 10-100 and the ZSM-12 has a silica to alumina ratio of 50-300.

15. A transalkylation process comprising:
supplying a first feed comprising toluene to a transalkylation reactor;
supplying a second feed comprising a C9 aromatic material and a C10 aromatic material to the transalkylation reactor; and
conducting a transalkylation reaction between the first feed and the second feed in the presence of a transalkylation catalyst comprising an aluminosilicate molecular sieve and a hydrogenation metal component under transalkylation conditions to produce a transalkylation reaction product mixture comprising at least one alicyclic compound,
wherein the transalkylation reaction is conducted under a first set of transalkylation conditions in a beginning phase of a transalkylation reactor operation cycle and a second set of transalkylation conditions after the beginning phase of the operation cycle;
wherein the first set of transalkylation conditions comprises a first ratio of the weight of the toluene to a total weight of the toluene, the C9 aromatic material, and the C10 aromatic material;
wherein the second set of transalkylation conditions comprises a second ratio of the weight of the toluene to the total weight of the toluene, the C9 aromatic material, and the C10 aromatic material; and
wherein the first ratio divided by the second ratio is between 1.5 and 3.0, such that ring-loss is reduced in the transalkylation process compared to a transalkylation process operated under the second set of transalkylation conditions only.

16. The process of claim 15, wherein the aluminosilicate molecular sieve comprises a first molecular sieve in a first catalyst bed and a second molecular sieve in a second catalyst bed; and
wherein conducting the transalkylation reaction comprises:
supplying the first feed and the second feed to the first molecular sieve to produce a first effluent; and
supplying the first effluent to the second molecular sieve.

17. The process of claim 16, wherein the first molecular sieve comprises ZSM-5 and the second molecular sieve comprises ZSM-12.

18. The process of claim 17, wherein the ZSM-5 has a silica to alumina ratio of 10-100 and the ZSM-12 has a silica to alumina ratio of 50-300.

* * * * *